(12) United States Patent
Sennett

(10) Patent No.: US 7,959,634 B2
(45) Date of Patent: Jun. 14, 2011

(54) ORTHOPEDIC SURGERY ACCESS DEVICES

(75) Inventor: Andrew R. Sennett, Hanover, MA (US)

(73) Assignee: Soteira Inc., Dedham, MA (US)

( * ) Notice: Subject to any disclaimer, the term of this patent is extended or adjusted under 35 U.S.C. 154(b) by 0 days.

(21) Appl. No.: 11/091,232

(22) Filed: Mar. 28, 2005

(65) Prior Publication Data
US 2005/0216018 A1    Sep. 29, 2005

Related U.S. Application Data

(60) Provisional application No. 60/557,246, filed on Mar. 29, 2004.

(51) Int. Cl.
*A61B 17/32* (2006.01)

(52) U.S. Cl. .................................................. 606/79

(58) Field of Classification Search .............. 606/180, 606/169–171, 79, 80; 604/24
See application file for complete search history.

(56) References Cited

U.S. PATENT DOCUMENTS

| | | | |
|---|---|---|---|
| 4,772,264 A | 9/1988 | Cragg | |
| 4,969,888 A | 11/1990 | Scholten et al. | |
| 5,015,255 A | 5/1991 | Kuslich | |
| 5,062,845 A | 11/1991 | Kuslich et al. | |
| 5,085,635 A | 2/1992 | Cragg | |
| 5,100,423 A | 3/1992 | Fearnot | |
| 5,108,404 A | 4/1992 | Scholten et al. | |
| 5,257,994 A | 11/1993 | Lin | |
| 5,269,785 A | 12/1993 | Bonutti | |
| 5,322,505 A * | 6/1994 | Krause et al. | 604/24 |
| 5,332,402 A | 7/1994 | Teitelbaum | |
| 5,342,371 A | 8/1994 | Welter et al. | |
| 5,370,653 A | 12/1994 | Cragg | |
| 5,397,310 A | 3/1995 | Chu et al. | |
| 5,405,377 A | 4/1995 | Cragg | |
| 5,437,665 A | 8/1995 | Munro | |
| 5,445,639 A | 8/1995 | Kuslich et al. | |
| 5,489,274 A | 2/1996 | Chu et al. | |
| 5,499,981 A | 3/1996 | Kordis | |

(Continued)

FOREIGN PATENT DOCUMENTS

NL      1009471 C      12/1999
(Continued)

OTHER PUBLICATIONS

Cavity Creation Curette Set, Website of AO Foundation (http://www.aofoundation.org) printed Feb. 13, 2006.
(Continued)

*Primary Examiner* — Eduardo C Robert
*Assistant Examiner* — David Comstock
(74) *Attorney, Agent, or Firm* — Goodwin Procter LLP

(57) ABSTRACT

The present invention provides instrumentation that facilitates access to both sides of the vertebral body from a single access point. More particularly, the present invention provides bendable access devices that can be steered so as to traverse the vertebral body from the point of entry into the vertebral body, through the cancellous bone within the vertebral body, and to the contralateral side of the vertebral body. This steerability is provided by forming the access device with a series of slots, grooves, or notches in the side of the access device near the distal end of the access device, which slots, grooves, or notches reduce the bending stiffness of the access device. As a result, the distal end of the access device bends as it is being advanced into the vertebral body.

16 Claims, 3 Drawing Sheets

U.S. PATENT DOCUMENTS

| | | | |
|---|---|---|---|
| 5,540,693 A | 7/1996 | Fisher | |
| 5,549,637 A | 8/1996 | Crainich | |
| 5,554,114 A | 9/1996 | Wallace et al. | |
| 5,645,566 A | 7/1997 | Brenneman et al. | |
| 5,665,115 A | 9/1997 | Cragg | |
| 5,683,448 A | 11/1997 | Cragg | |
| 5,695,513 A * | 12/1997 | Johnson et al. | 606/180 |
| 5,716,365 A | 2/1998 | Goicoechea et al. | |
| 5,752,969 A | 5/1998 | Cunci et al. | |
| 5,766,237 A | 6/1998 | Cragg | |
| 5,776,180 A | 7/1998 | Goicoechea et al. | |
| 5,782,861 A | 7/1998 | Cragg et al. | |
| 5,795,331 A | 8/1998 | Cragg et al. | |
| 5,807,330 A | 9/1998 | Teitelbaum | |
| 5,814,044 A | 9/1998 | Hooven | |
| 5,868,762 A | 2/1999 | Cragg et al. | |
| 5,916,263 A | 6/1999 | Goicoechea et al. | |
| 5,928,239 A | 7/1999 | Mirza | |
| 5,957,884 A | 9/1999 | Hooven | |
| 5,984,950 A | 11/1999 | Cragg et al. | |
| 5,989,223 A | 11/1999 | Chu et al. | |
| 6,051,020 A | 4/2000 | Goicoechea et al. | |
| 6,063,069 A | 5/2000 | Cragg et al. | |
| 6,071,300 A | 6/2000 | Brenneman et al. | |
| 6,071,301 A | 6/2000 | Cragg et al. | |
| 6,073,051 A * | 6/2000 | Sharkey et al. | 607/99 |
| 6,086,607 A | 7/2000 | Cragg et al. | |
| 6,096,021 A | 8/2000 | Helm et al. | |
| 6,117,167 A | 9/2000 | Goicoechea et al. | |
| 6,146,373 A | 11/2000 | Cragg et al. | |
| 6,162,192 A | 12/2000 | Cragg et al. | |
| 6,174,328 B1 | 1/2001 | Cragg | |
| 6,200,328 B1 | 3/2001 | Cragg et al. | |
| 6,203,779 B1 | 3/2001 | Ricci et al. | |
| 6,235,043 B1 | 5/2001 | Reiley et al. | |
| 6,248,110 B1 | 6/2001 | Reiley et al. | |
| 6,261,293 B1 | 7/2001 | Nicholson et al. | |
| 6,302,906 B1 | 10/2001 | Goicoechea et al. | |
| 6,303,100 B1 | 10/2001 | Ricci et al. | |
| 6,315,753 B1 | 11/2001 | Cragg et al. | |
| 6,315,789 B1 | 11/2001 | Cragg | |
| 6,371,974 B1 | 4/2002 | Brenneman et al. | |
| 6,383,188 B2 | 5/2002 | Kuslich et al. | |
| 6,387,122 B1 | 5/2002 | Cragg | |
| 6,440,138 B1 | 8/2002 | Reiley et al. | |
| 6,440,151 B1 | 8/2002 | Cragg et al. | |
| 6,440,153 B2 | 8/2002 | Cragg et al. | |
| 6,447,534 B2 | 9/2002 | Cragg et al. | |
| 6,475,466 B1 | 11/2002 | Ricci et al. | |
| 6,511,468 B1 | 1/2003 | Cragg et al. | |
| 6,527,734 B2 | 3/2003 | Cragg et al. | |
| 6,533,751 B2 | 3/2003 | Cragg et al. | |
| 6,544,236 B1 | 4/2003 | Cragg et al. | |
| 6,558,367 B1 | 5/2003 | Cragg et al. | |
| 6,558,386 B1 | 5/2003 | Cragg | |
| 6,558,390 B2 | 5/2003 | Cragg | |
| 6,575,979 B1 | 6/2003 | Cragg | |
| 6,582,467 B1 | 6/2003 | Teitelbaum et al. | |
| 6,610,026 B2 | 8/2003 | Cragg et al. | |
| 6,635,027 B1 | 10/2003 | Cragg et al. | |
| 6,679,886 B2 | 1/2004 | Weikel et al. | |
| 6,692,459 B2 | 2/2004 | Teitelbaum | |
| 6,709,435 B2 | 3/2004 | Lin | |
| 6,740,090 B1 | 5/2004 | Cragg et al. | |
| 6,746,451 B2 | 6/2004 | Middleton et al. | |
| 6,749,614 B2 | 6/2004 | Teitelbaum et al. | |
| 6,786,903 B2 | 9/2004 | Lin | |
| 6,790,210 B1 | 9/2004 | Cragg et al. | |
| 6,796,988 B2 | 9/2004 | Melkent et al. | |
| 6,805,697 B1 | 10/2004 | Helm et al. | |
| 6,821,277 B2 | 11/2004 | Teitelbaum | |
| 6,824,087 B2 | 11/2004 | McPherson et al. | |
| 6,849,086 B2 | 2/2005 | Cragg | |
| 6,863,672 B2 | 3/2005 | Reiley et al. | |
| 6,875,212 B2 | 4/2005 | Shaolian et al. | |
| 6,875,219 B2 | 4/2005 | Arramon et al. | |
| 6,896,677 B1 | 5/2005 | Lin et al. | |
| 6,899,713 B2 | 5/2005 | Shaolian et al. | |
| 6,899,716 B2 | 5/2005 | Cragg | |
| 6,921,403 B2 | 7/2005 | Cragg et al. | |
| 6,964,657 B2 | 11/2005 | Cragg et al. | |
| 6,964,667 B2 | 11/2005 | Shaolian et al. | |
| 6,984,219 B2 | 1/2006 | Ashby et al. | |
| 7,008,424 B2 | 3/2006 | Teitelbaum | |
| 7,014,633 B2 | 3/2006 | Cragg | |
| 7,037,323 B2 | 5/2006 | Sing et al. | |
| 7,048,710 B1 | 5/2006 | Cragg et al. | |
| 7,083,621 B2 | 8/2006 | Shaolian et al. | |
| 7,087,055 B2 | 8/2006 | Lim et al. | |
| 7,087,058 B2 | 8/2006 | Cragg | |
| 7,131,605 B2 | 11/2006 | McPherson et al. | |
| 7,135,021 B2 | 11/2006 | Lin et al. | |
| 7,175,646 B2 | 2/2007 | Brenneman et al. | |
| 7,192,436 B2 | 3/2007 | Sing et al. | |
| 7,201,725 B1 | 4/2007 | Cragg et al. | |
| 7,241,297 B2 | 7/2007 | Shaolian et al. | |
| 7,309,338 B2 | 12/2007 | Cragg | |
| 7,318,826 B2 | 1/2008 | Teitelbaum et al. | |
| 7,329,259 B2 | 2/2008 | Cragg | |
| 7,329,268 B2 | 2/2008 | Van Nguyen et al. | |
| 2001/0034509 A1 | 10/2001 | Cragg et al. | |
| 2001/0041913 A1 | 11/2001 | Cragg et al. | |
| 2001/0049527 A1 | 12/2001 | Cragg | |
| 2001/0056254 A1 | 12/2001 | Cragg et al. | |
| 2002/0010442 A1 | 1/2002 | Teitelbaum | |
| 2002/0016583 A1 | 2/2002 | Cragg | |
| 2002/0016611 A1 | 2/2002 | Cragg et al. | |
| 2002/0019659 A1 | 2/2002 | Goicoechea et al. | |
| 2002/0022822 A1 | 2/2002 | Cragg et al. | |
| 2002/0034493 A1 | 3/2002 | Ricci et al. | |
| 2002/0062104 A1 | 5/2002 | Ashby et al. | |
| 2002/0062106 A1 | 5/2002 | Chu et al. | |
| 2002/0068975 A1 | 6/2002 | Teitelbaum et al. | |
| 2002/0082598 A1 | 6/2002 | Teitelbaum | |
| 2002/0082600 A1 | 6/2002 | Shaolian et al. | |
| 2002/0091372 A1 | 7/2002 | Cragg et al. | |
| 2002/0116051 A1 | 8/2002 | Cragg | |
| 2002/0156495 A1 | 10/2002 | Brenneman et al. | |
| 2002/0173796 A1 | 11/2002 | Cragg | |
| 2002/0188300 A1 | 12/2002 | Arramon et al. | |
| 2002/0198526 A1 | 12/2002 | Shaolian et al. | |
| 2003/0040733 A1 | 2/2003 | Cragg et al. | |
| 2003/0050644 A1 | 3/2003 | Boucher et al. | |
| 2003/0068296 A1 | 4/2003 | Ricci et al. | |
| 2003/0088271 A1 | 5/2003 | Cragg et al. | |
| 2003/0135237 A1 | 7/2003 | Cragg et al. | |
| 2003/0158557 A1 | 8/2003 | Cragg et al. | |
| 2003/0187433 A1 | 10/2003 | Lin | |
| 2003/0191474 A1 | 10/2003 | Cragg et al. | |
| 2003/0195518 A1 | 10/2003 | Cragg | |
| 2003/0204189 A1 | 10/2003 | Cragg | |
| 2003/0225391 A1 | 12/2003 | Cragg et al. | |
| 2003/0229353 A1 | 12/2003 | Cragg | |
| 2004/0006341 A1 | 1/2004 | Shaolian et al. | |
| 2004/0006344 A1 | 1/2004 | Nguyen et al. | |
| 2004/0073139 A1 | 4/2004 | Hirsch et al. | |
| 2004/0073287 A1 | 4/2004 | Goicoechea et al. | |
| 2004/0082954 A1 | 4/2004 | Teitelbaum et al. | |
| 2004/0082961 A1 | 4/2004 | Teitelbaum | |
| 2004/0087950 A1 | 5/2004 | Teitelbaum | |
| 2004/0092933 A1 | 5/2004 | Shaolian et al. | |
| 2004/0092988 A1 | 5/2004 | Shaolian et al. | |
| 2004/0092993 A1 | 5/2004 | Teitelbaum et al. | |
| 2004/0098086 A1 | 5/2004 | Goicoechea et al. | |
| 2004/0098115 A1 | 5/2004 | Goicoechea et al. | |
| 2004/0102774 A1 | 5/2004 | Trieu | |
| 2004/0106940 A1 | 6/2004 | Shaolian et al. | |
| 2004/0106979 A1 | 6/2004 | Goicoechea et al. | |
| 2004/0133280 A1 | 7/2004 | Trieu | |
| 2004/0158287 A1 | 8/2004 | Cragg et al. | |
| 2004/0162559 A1 | 8/2004 | Arramon et al. | |
| 2004/0167599 A1 | 8/2004 | Goicoechea et al. | |
| 2004/0176723 A1 | 9/2004 | Sing et al. | |
| 2004/0181191 A1 | 9/2004 | Teitelbaum | |
| 2004/0210297 A1 | 10/2004 | Lin et al. | |
| 2004/0215190 A1 | 10/2004 | Nguyen et al. | |
| 2004/0215193 A1 | 10/2004 | Shaolian et al. | |

| | | |
|---|---|---|
| 2004/0220577 A1 | 11/2004 | Cragg et al. |
| 2004/0220615 A1 | 11/2004 | Lin et al. |
| 2005/0033292 A1 | 2/2005 | Teitelbaum et al. |
| 2005/0033360 A1 | 2/2005 | Sing et al. |
| 2005/0038432 A1 | 2/2005 | Shaolian et al. |
| 2005/0038514 A1 | 2/2005 | Helm et al. |
| 2005/0043737 A1 | 2/2005 | Reiley et al. |
| 2005/0070908 A1 | 3/2005 | Cragg |
| 2005/0113843 A1 | 5/2005 | Arramon |
| 2005/0113919 A1 | 5/2005 | Cragg et al. |
| 2005/0113928 A1 | 5/2005 | Cragg et al. |
| 2005/0113929 A1 | 5/2005 | Cragg et al. |
| 2005/0124999 A1 | 6/2005 | Teitelbaum et al. |
| 2005/0131529 A1 | 6/2005 | Cragg |
| 2005/0137601 A1 | 6/2005 | Assell et al. |
| 2005/0137602 A1 | 6/2005 | Assell et al. |
| 2005/0137604 A1 | 6/2005 | Assell et al. |
| 2005/0137605 A1 | 6/2005 | Assell et al. |
| 2005/0137607 A1 | 6/2005 | Assell et al. |
| 2005/0137612 A1 | 6/2005 | Assell et al. |
| 2005/0149022 A1 | 7/2005 | Shaolian et al. |
| 2005/0149034 A1 | 7/2005 | Assell et al. |
| 2005/0149049 A1 | 7/2005 | Assell et al. |
| 2005/0149191 A1 | 7/2005 | Cragg et al. |
| 2005/0165406 A1 | 7/2005 | Assell et al. |
| 2005/0170120 A1 | 8/2005 | Teitelbaum et al. |
| 2005/0182417 A1 | 8/2005 | Pagano |
| 2005/0228417 A1 | 10/2005 | Teitelbaum et al. |
| 2005/0234453 A1 | 10/2005 | Shaolian et al. |
| 2005/0251140 A1 | 11/2005 | Shaolian et al. |
| 2005/0261684 A1 | 11/2005 | Shaolian et al. |
| 2005/0261689 A1 | 11/2005 | Lin |
| 2005/0261695 A1 | 11/2005 | Cragg et al. |
| 2006/0036276 A1 | 2/2006 | Nguyen et al. |
| 2006/0058800 A1 | 3/2006 | Ainsworth et al. |
| 2006/0064101 A1 | 3/2006 | Arramon |
| 2006/0116690 A1 | 6/2006 | Pagano |
| 2006/0133193 A1 | 6/2006 | Arramon |
| 2006/0142779 A1 | 6/2006 | Arramon et al. |
| 2006/0142795 A1 | 6/2006 | Nguyen et al. |
| 2006/0164913 A1 | 7/2006 | Arramon |
| 2006/0184188 A1 | 8/2006 | Li et al. |
| 2006/0206209 A1 | 9/2006 | Cragg et al. |
| 2006/0235425 A1 | 10/2006 | Lin et al. |
| 2006/0264957 A1 | 11/2006 | Cragg et al. |
| 2007/0010717 A1 | 1/2007 | Cragg |
| 2007/0016194 A1 | 1/2007 | Shaolian et al. |
| 2007/0055260 A1 | 3/2007 | Cragg |
| 2007/0066977 A1 | 3/2007 | Assell et al. |
| 2007/0100367 A1 | 5/2007 | Quijano et al. |
| 2007/0100368 A1 | 5/2007 | Quijano et al. |
| 2007/0100369 A1 | 5/2007 | Cragg et al. |
| 2007/0149994 A1 | 6/2007 | Sosnowski et al. |
| 2007/0213827 A1 | 9/2007 | Arramon |
| 2007/0233099 A1 | 10/2007 | Cragg |
| 2007/0233260 A1 | 10/2007 | Cragg |
| 2007/0260270 A1 | 11/2007 | Assell et al. |
| 2007/0265697 A1 | 11/2007 | Goicoechea et al. |
| 2007/0282373 A1 | 12/2007 | Ashby et al. |
| 2008/0004707 A1 | 1/2008 | Cragg et al. |
| 2008/0045881 A1 | 2/2008 | Teitelbaum et al. |
| 2008/0045922 A1 | 2/2008 | Cragg et al. |
| 2008/0065076 A1 | 3/2008 | Cragg et al. |
| 2008/0065080 A1 | 3/2008 | Assell et al. |
| 2008/0065092 A1 | 3/2008 | Assell et al. |
| 2008/0065093 A1 | 3/2008 | Assell et al. |
| 2008/0065094 A1 | 3/2008 | Assell et al. |
| 2008/0071278 A1 | 3/2008 | Assell et al. |
| 2008/0071282 A1 | 3/2008 | Assell et al. |

FOREIGN PATENT DOCUMENTS

| | | |
|---|---|---|
| WO | WO-93/04634 | 3/1993 |
| WO | WO-03/101308 | 12/2003 |

OTHER PUBLICATIONS

Chiu et al. (2005) "Percutaneous Vertebral Augmentation and Reconstruction with an Intravertebral Mesh and Morcelized Bone Graft," The Internet Journal of Spine Surgery (website: http://www.ispub.com/ostia/index.php?xmlFilePath=journals/ijss/vol2n1/spine.xml) printed Oct. 4, 2007.

Lam et al. (2005) "A Novel Percutaneous System for Bone Graft Delivery and Containment for Elevation and Stabilization of Vertebral Compression Fractures," Neurosurg Focus 18(3):1-7.

OptiMesh 500E Extrapedicular Surgical Technique for Vertebral Stabilization (Handbook) Spineology pp. 1-24, Jun. 24, 2003.

Vallejo et al. (2006) "Percutaneous Cement Injection into a Created Cavity for the Treatment of Vertebral Body Fracture," Clin. J. Pain. 22:182-89.

Verdult, E.P.H.A., *"Drilling Back: Design of a Directional Drilling Device and Development of a New Spinal Anchoring Technique,"* Techniche Universiteit Te Delft (1998).

Supplementary European Search Report for EP 05751822.7 issued Dec. 8, 2008.

\* cited by examiner

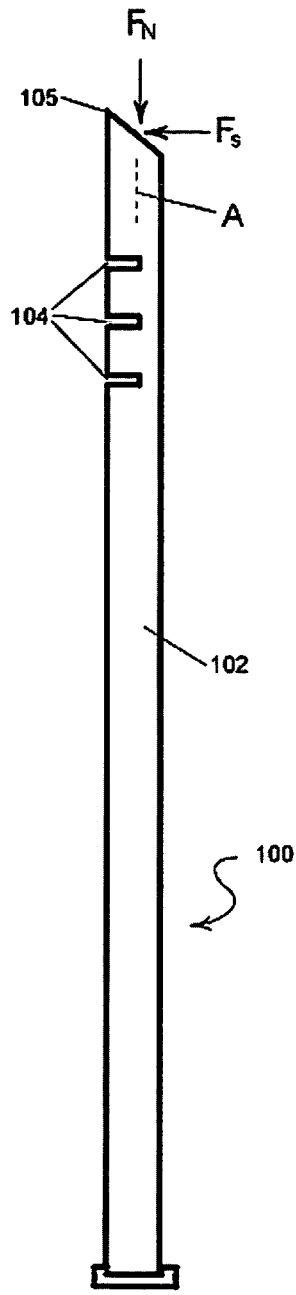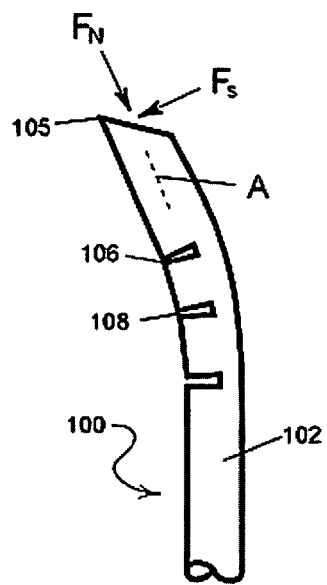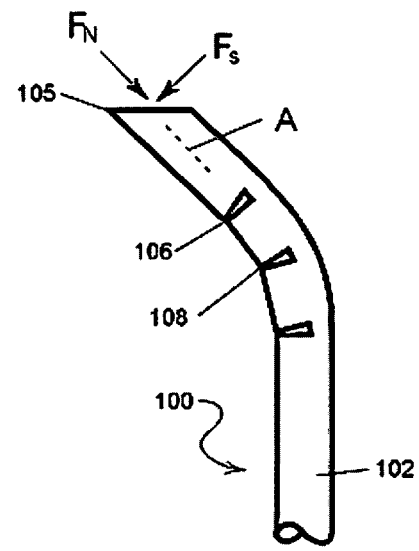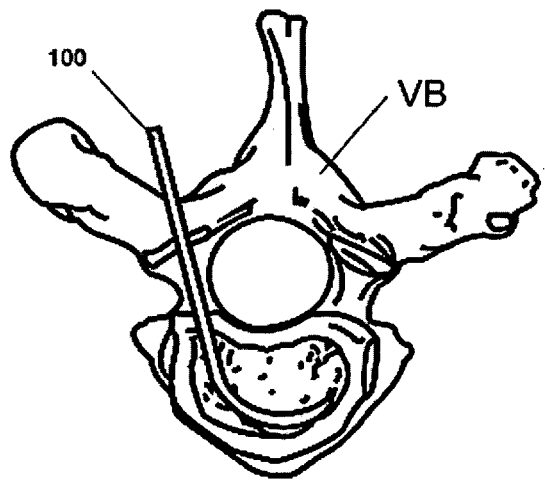
FIGURE 1
FIGURE 2
FIGURE 3
FIGURE 4

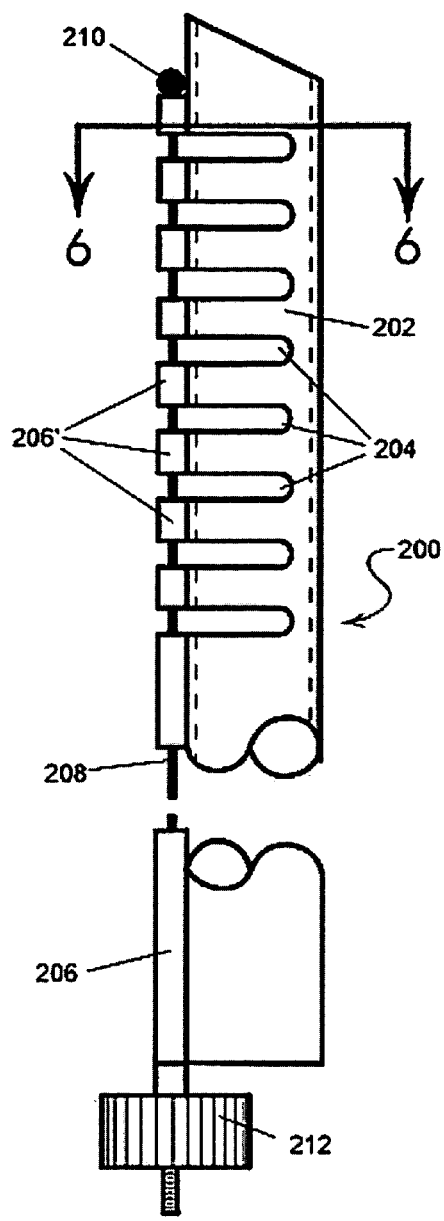
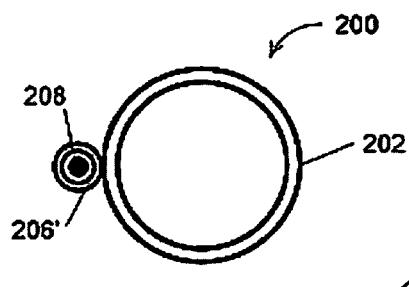
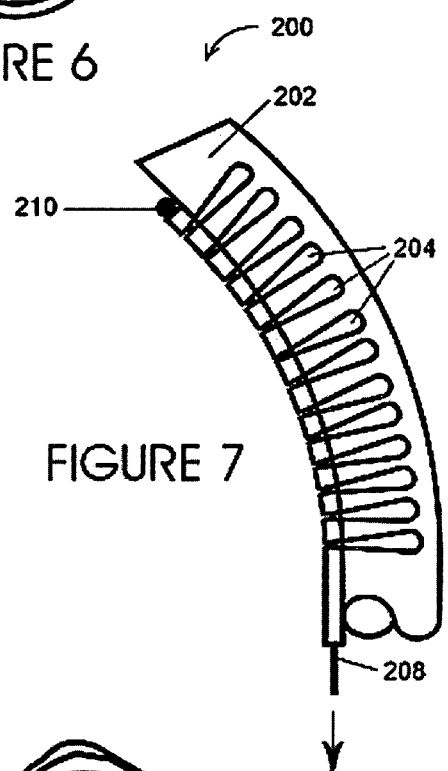
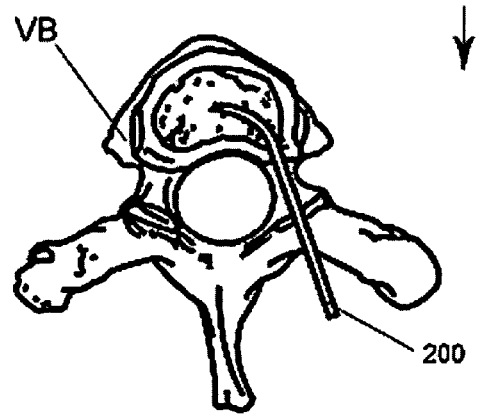
FIGURE 5
FIGURE 6
FIGURE 7
FIGURE 8

ORTHOPEDIC SURGERY ACCESS DEVICES

CROSS-REFERENCE TO RELATED APPLICATIONS

This application claims priority benefit of provisional patent application Ser. No. 60/557,246 filed Mar. 29, 2004, the contents of which are incorporated by reference.

FIELD OF THE INVENTION

In general, the invention relates to instrumentation used during minimally invasive orthopedic surgery. More particularly, the invention relates to instruments used to create the initial access passageway into the skeletal structure being treated.

BACKGROUND OF THE INVENTION

There are many disease states and abnormal conditions that cause defects in the skeleton. For instance, osteoporosis and other metabolic bone conditions weaken the bone structure and predispose the bone to fracture. These same diseases also impair and prolong healing, which can lead to the formation of bone defects. If not treated, certain fractures and bone defects may progress and lead to the development of severe neurological or other medical complications.

Other examples of bone defects are those resulting from the excision of benign or malignant lesions of the skeleton. Removal of tumors often compromises the structural integrity of the bone structure and thus requires surgical stabilization and filling of the defects with biological materials such as bone grafts or cements.

Bone defects also result from bone grafting procedures, wherein the patient's own bone is transplanted to another region of the skeleton. Healing of the defect is often retarded and painful, necessitating further treatment including filling the defect with bone substitute materials to induce healing. If not repaired, the defect may worsen or fracture due to the compromise of structural integrity of the bone.

One approach to treating many bone defects comprises injecting, packing, or filling the defect with biocompatible bone cement. Such bone cements are generally formulations of non-resorbable biocompatible polymers such as PMMA (polymethylmethacrylate) or resorbable calcium phosphate or calcium sulphate cement. These cements allow the gradual replacement of the cement with living bone. Bone cements have been used successfully in the treatment of bone defects secondary to compression fractures of the distal radius, the calcaneous, the tibial plateau, and the vertebral body.

Historically, however, most applications of bone cements have been limited to open procedures in which the surgeon injects, packs, or tamps the biological material under direct visualization of the defect margins. Although direct visualization maximally allows the surgeon to identify adjacent structures that may be compromised by the inadvertent placement or injection of cement, less invasive means (apparatus and techniques) to assist the surgeon in safely and effectively placing biocompatible cements are generally desirable.

For example, one debilitating condition for which less invasive means to treat with injectable cement would be desirable is osteoporotic compression fracture of the spine. More than 700,000 osteoporotic compression fractures of the vertebrae occur each year in the United States—primarily in the elderly female population. Until recently, treatment of such fractures was limited to conservative, non-operative therapies such as bed rest, bracing, and medications.

A relatively new procedure known as "vertebroplasty" was developed in the mid 1980's to address the inadequacy of conservative treatment for vertebral body fracture. This procedure involves injecting radio-opaque bone cement directly into the fracture void through a minimally invasive cannula or needle under fluoroscopic control. The cement is pressurized by a syringe or similar plunger mechanism, thus causing the cement to fill the void and penetrate the interstices of broken trabecular bone. Once cured, the cement stabilizes the fracture and reduces pain—usually dramatically and immediately.

An alternative technique which has gained popularity in recent years is a modified vertebroplasty technique in which a "balloon tamp" is inserted into the vertebral body via a cannula approach to expand the fractured bone and create a void within the cancellous structure. The tamping effect is caused by the inflation of a balloon membrane that expands, thereby producing radial force. When subsequently deflated, the membrane leaves a void that is then filled with bone cement.

Regardless of which of these (or other) techniques is used when correcting defects within the vertebral body, it is generally desirable to inject cement substantially symmetrically or bilaterally to strengthen the entire vertebral body. In order to treat bilaterally, separate approaches to and access into the vertebral body have needed to be made from either side of the spine. Even for the simplest procedures, however, such vertebral approach and access requires skilled, delicate, time-consuming placement of the surgical instruments. Therefore, instrumentation and techniques that would facilitate surgical access to both sides of the vertebral body via a single approach is desirable.

SUMMARY OF THE INVENTION

The present invention provides instrumentation that facilitates access to both sides of the vertebral body from a single access point. More particularly, the present invention provides bendable access devices that can be steered so as to traverse the vertebral body from the point of entry into the vertebral body, through the cancellous bone within the vertebral body, and to the contralateral side of the vertebral body. This steerability is provided by forming the access device with a series of slots, grooves, or notches in the side of the access device near the distal end of the access device, which slots, grooves, or notches reduce the bending stiffness of the access device. As a result, the distal end of the access device bends as it is being advanced into the vertebral body.

According to one embodiment, the access device comprises a solid or hollow shaft, preferably having a beveled tip which imparts a side load when the tip encounters more solid bone. According to another embodiment, the access device includes an actuating member, e.g., a wire that is anchored at the distal end of the access device and that extends along a side or within the center of the access device; pulling on the proximal end of the wire causes the distal end of the access device to curve laterally and move into the soft, cancellous bone. According to a third embodiment of the invention, more than one group of slots or notches is provided, with the separate groups being circumferentially offset relative to each other; this allows the access device to bend or steer in more than just a single plane.

Furthermore, since it may be desirable to use a hollow needle to inject bone cement into the vertebral body, hollow embodiments of the invention may be covered with a thin, flexible polymeric coating or shrink tube covering that does not increase the bending stiffness of the structure. The coating or shrink tube covering forms a tube to allow cement to flow through the access device to the distal most end of the access device without leakage.

The access device may be constructed so that its distal end is initially straight. Alternatively, the access device may be preformed with a nominal amount of initial curvature, so that the slots facilitate bending of the access device into a second, smaller-radiused curvature.

BRIEF DESCRIPTION OF THE DRAWINGS

The invention will now be described in greater detail in connection with the drawings, in which:

FIGS. 1-3 are side elevation views of a first embodiment of an access device according to the invention, illustrating progressively bending of the distal tip thereof;

FIG. 4 is a view in the transverse plane of a vertebral body, illustrating the access device shown in FIGS. 1-3 entering and curving through the vertebral body;

FIGS. 5 and 7 are side elevation views of a second embodiment of an access device according to the invention, illustrating progressively bending of the distal tip thereof, with FIG. 6 being a section view of the access as taken along lines 6-6 in FIG. 5;

FIG. 8 is a view in the transverse plane of a vertebral body, illustrating the access device shown in FIGS. 5-7 entering and curving through the vertebral body.

DETAILED DESCRIPTION

Figure 9:
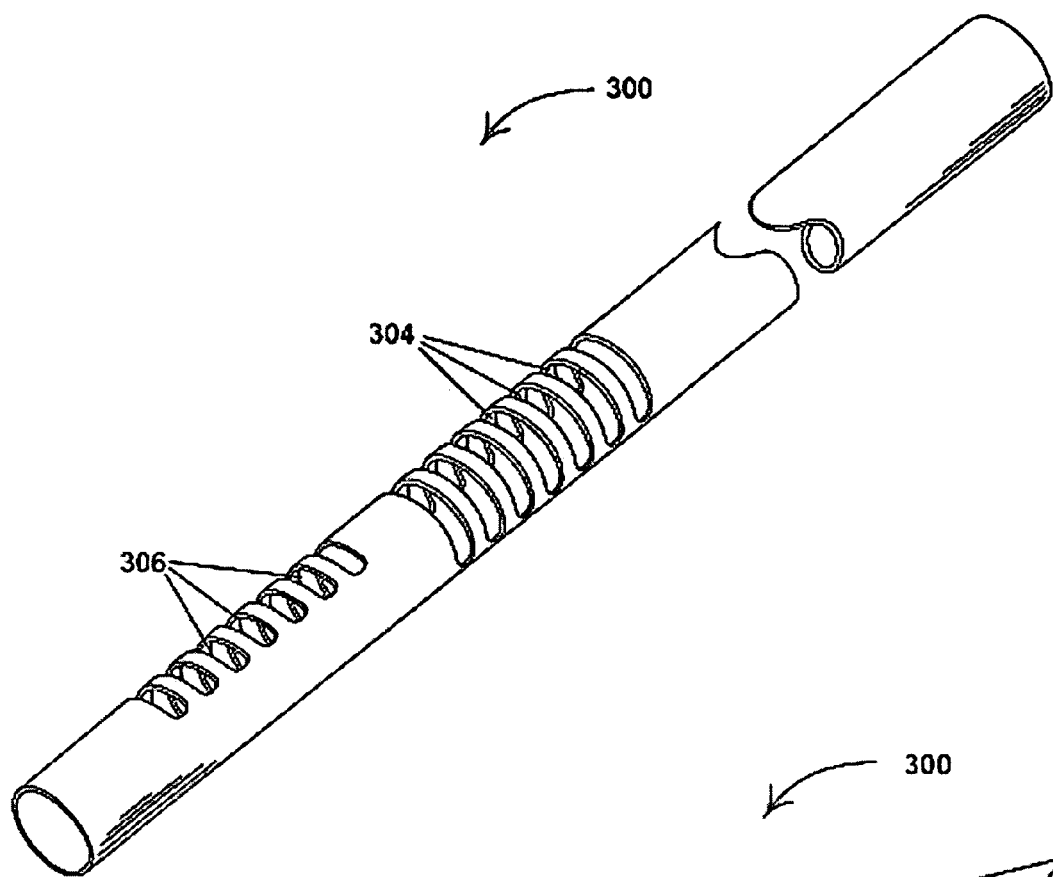
FIGS. 9 and 10 are a side view and a perspective view of a third embodiment of an access device according to the invention, in which the distal end of the access device curves in multiple planes simultaneously.

A first access device 100 according to the invention is illustrated in FIGS. 1-4. The access device 100, which allows access to the contralateral side of the vertebral body from a single intrapedicular access point, is a buckling needle, guide wire, or trocar that alters its shape from straight to curved through the action of engineered buckling zones to permit bilateral vertebral access.

In the prior art, certain needle trocars have had angled bevel points. When the point contacts a solid material as the trocar is being advanced through tissue, a side load is induced on the needle, thereby causing it to deflect. Typically, this deflection is effected by light mallet strikes to the proximal end of the trocar, wherein the shock load transfers down the stiff shaft of the trocar. Continued advance of the trocar causes the needle as a whole to deflect according to the position of the bevel; the trocar itself, however, remains essentially straight, and it simply follows an altered course or vector through the tissue. As a result, such angled bevel point trocars have not afforded full bilateral access to the vertebral body from a single access point.

According to the invention, however, a "segmented" trocar 100 is provided in which the shaft of the trocar buckles preferentially upon mallet impact, with the trocar segments buckling from the least stiff segment first to the stiffest segment last. As illustrated in FIGS. 1-3, the shaft 102 of the trocar 100, which may be solid or hollow, has a number of slots or notches 104 (e.g., three or more) formed in its side at discrete locations near its distal end such that the bending stiffness of the shaft is reduced at the location of each of the slots or notches 104. Therefore, when the tip 105 of the trocar 100 encounters solid material (e.g., cortical bone tissue) and the normal force $F_N$ induces a side load $F_S$ on the tip of the trocar 100, the shaft collapses slightly, initially at the least stiff slot 106, thereby changing the axis A of the tip of the trocar shaft so that it is no longer co-axial with the remainder of the shaft. With continued impact and deflection of the distal end of the shaft, the slot 106 eventually closes completely as illustrated in FIG. 2, thus stiffening the segment and preventing further deflection of that section of the needle, trocar, or guide wire. Once the least stiff segment has collapsed shut, a second segment, now possessing the least stiffness because of its own slot (e.g., slot 108) preferentially deflects upon continued loading.

Depending on the number of slots and the bending stiffness of the trocar at the slots, the needle alters its vector and curves into the desired location within the vertebral body VB, as illustrated in FIG. 4. Depending on the desired size of the channel into the vertebral body VB, deflecting needles of increasing diameter or different radii of curvature may be introduced. These subsequently placed needles may be hollow, to be advanced into the vertebral body over an initial, solid needle, or they may be solid. Depending on the rotational orientation of the needle bevel at the tip 105 and the orientation of the slots 104, the needle trocar 100 of the invention can be deflected in any plane desired by the surgeon. Therefore, by using a series of light mallet strikes, the needle 100 may be guided in a curving path across the vertebral body, from the side from which the vertebral body is accessed across to the contralateral side of the vertebral body. This facilitates subsequent introduction of further access devices and emplacement of vertebral stabilization devices in a generally symmetrical orientation vis-a-vis the sagital midline of the vertebral body.

The slotted or notched needles may be prevented from deflecting during advancement by first inserting them in a protective, rigid tube. Conversely, the slotted tubes may be prevented from deflecting during advancement by first inserting a rigid wire inside the tube, fully to the end. These rigid components may be selectively removed by the surgeon when deflection of the tip during advancement is the desired clinical result.

Another embodiment 200 of a deflectable, curving needle used to access the site of bone repair is illustrated in FIGS. 5-8. This embodiment 200 is somewhat similar to the embodiment 100 illustrated in FIGS. 1-4 and described above. With this embodiment 200, the needle or cannula 202, which may be hollow (as illustrated) or solid, is first fully inserted to a desired depth of penetration within the vertebral body VB, then deflected into a curved orientation or configuration (as shown in FIG. 8) by generating a bending moment along the side of the shaft or cannula.

The cannula or needle shaft 202 is preferably constructed of a tubular or solid superelastic memory alloy such as nitinol and has a series of slots 204 laser-cut or micro-machined into its side to reduce bending stiffness along the tip. A second, smaller-diameter tube 206 is joined to the shaft 202 by welding or other joining method, prior to cutting the slots 204, and after slotting is configured as a series of tube segments 206' in the region of the tip of the cannula or needle shaft 202. The smaller tube and tube segments 206, 206' contain a wire or cable 208 that is affixed, e.g., by welding or melting its end into a bead 210, to the flexible, distal end of the tube 202 and to a movable fastener 212 (e.g., an internally threaded nut that mates with external threads at the proximal end of the wire or cable 208) at the other, proximal end of the device such that the length of wire or cable running along the side of the shaft 202 can be altered by means of the movable fastener 212. When the effective cable length is shortened, the tube or shaft 202 collapses in a manner that closes a plurality of the slots 204 on one side of the device, as illustrated in FIG. 7.

When actuated, the cannula or shaft 200 generates a side load as it curves or steers to one side. The amount of side load generated is proportional to the axial load placed on the cable 208. Since osteoporotic bone is significantly weakened by disease, and since the strength of the bone is naturally weakest in the transverse plane, the cannula or shaft will easily deflect within the weakened structure to position the tip of the needle across the midline of the vertebral body VB, into the contralateral, anterior one-third portion of the VB. Preferably, the cannula or shaft is made of radio-opaque materials; therefore, the position of the tip is easily visualized and optimized by the surgeon.

In the embodiments of the invention 100 and 200 described above, the slots in the cannula or shaft are axially aligned. As a result, the access devices 100, 200 bend or curve within a single plane. At times, however, it may be desirable for the access device of the invention to curve in multiple planes. For example, it is not uncommon to approach the vertebral body being treated from a cephalad to caudad (downward) approach angle in order to position the needle tip below the fracture plane of the collapsed vertebral body. Once the vertebral body is accessed, however, curving penetration through the vertebral body should be made along the transverse plane, in which the vertebral body lies.

Figure 10:
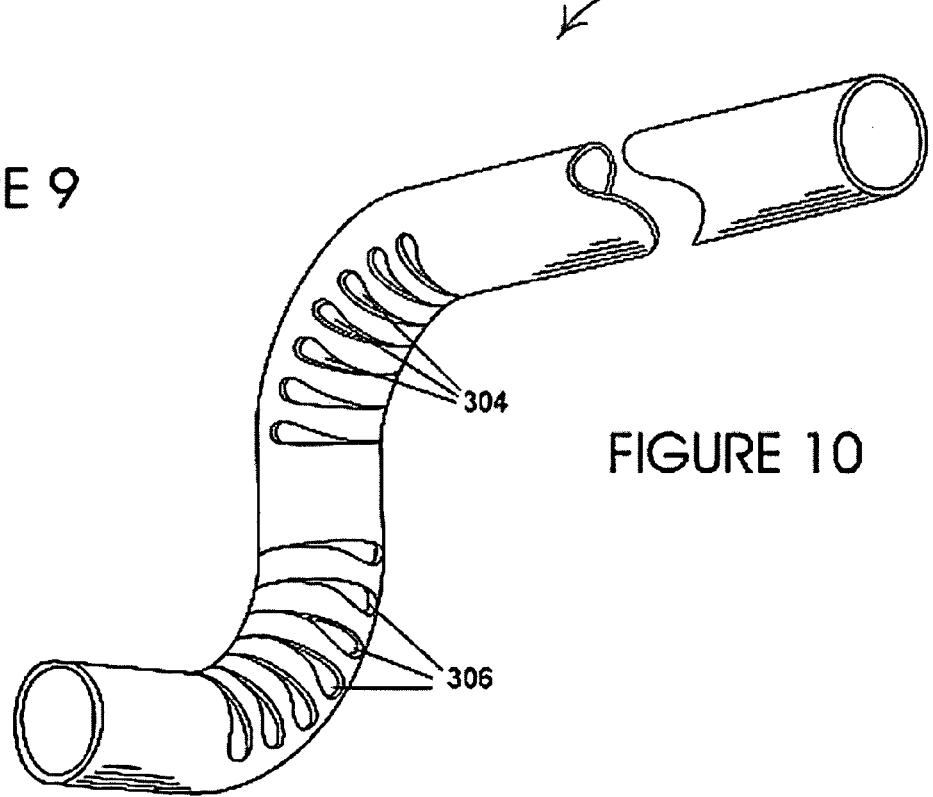

To provide the ability to curve in more than one plane, a further embodiment of the invention 300, illustrated in FIGS. 9 and 10 has multiple sets of slots or notches 304 and 306. In contrast to the notches 104 and 204 of the embodiments described above, in which the slots are all axially aligned with each other, in the embodiment 300, the notches 306 are circumferentially positioned 90° out of alignment with the notches 304. This feature allows the distal end of the access device 300 to curve in more than one plane simultaneously, e.g., in the XY and YZ planes, as illustrated in FIG. 10.

Once the desired region of the vertebral body VB has been accessed, the access device 100 or 200 is withdrawn and the vertebral body is further prepared for remedial fixation.

It will be appreciated that the described embodiments are illustrative of the invention, and that other embodiments within the scope of the invention will occur to those having skill in the art. The above-disclosed embodiments and such other embodiments are deemed to be within the scope of the following claims:

I claim:

1. A device for piercing a cortical wall and initiating access to a cancellous interior of a vertebral body via minimally invasive, percutaneous approach to the vertebral body, said device comprising:
    a hollow shaft comprising an elongate axis, said shaft having a proximal end and a distal end with a first series of notches or slots in a side of said shaft near said distal end, wherein said shaft has sufficient strength and rigidity, when restrained by a rigid element inserted within the hollow shaft, to remain essentially straight and to pierce the cortical wall of said vertebral body, and
    wherein said shaft comprises a preformed curvature near the distal end of the shaft such that a portion of said elongate axis at said distal end of said shaft is not co-axial with a portion of said elongate axis along a remainder of said shaft, when said shaft is unrestrained by said rigid element.

2. The device of claim 1, wherein said distal end has a beveled tip which facilitates lateral, curving deflection of said distal end.

3. The device of claim 1, further comprising an actuating member extending along a side of said shaft.

4. The device of claim 3, wherein said actuating member comprises a cable or wire that is tethered at said distal end, whereby pulling of said cable or wire in the direction of said proximal end causes lateral, curving deflection of said shaft.

5. The device of claim 1, further comprising a second series of notches or slots in a side of said shaft near said distal end, said second series of notches or slots being circumferentially offset relative to said first series of notches or slots.

6. The device of claim 1, further comprising a thin-walled flexible membrane covering said first series of slots or notches.

7. The device of claim 1, wherein the hollow shaft comprises an elastic memory material.

8. The device of claim 1, further comprising the rigid element, wherein:
    the rigid element is adapted to straighten the distal end of the hollow shaft when inserted therein; and
    the rigid element is adapted to allow the distal end of the hollow shaft to return to the preformed curvature when removed therefrom.

9. An apparatus for creating a channel in a vertebral body, the apparatus comprising:
    a rigid first element comprising a first elongate axis, said first rigid element having a proximal end and a distal end; and
    at least one hollow second element comprising a second elongate axis, said hollow second element comprising a plurality of slots near a distal end thereof, wherein the plurality of slots facilitates bending of the at least one hollow second element, wherein the at least one hollow second element is adapted to advance over the rigid first element, and wherein at least one of said distal end of said rigid first element and said distal end of said hollow second element comprises a preformed curvature, wherein said preformed curvature comprises a portion of an elongate axis of an element being non co-axial with a remainder of said elongate axis, when unrestrained by said rigid first element.

10. The apparatus of claim 9, wherein the rigid first element is solid.

11. The apparatus of claim 9, wherein the rigid first element comprises a wire.

12. The apparatus of claim 9, wherein at least one of the rigid first element and hollow second element comprise an elastic memory material.

13. The apparatus of claim 9, wherein at least one of the plurality of slots is circumferentially offset from at least one other slot.

14. The apparatus of claim 9, wherein at least one of the distal end of the rigid first element and the distal end of the hollow second element is configured for advancement through a rigid tube into the vertebral body.

15. The apparatus of claim 9, comprising at least two hollow second elements.

16. The apparatus of claim 9, wherein the distal end of at least one of the rigid first element and the second element is initially straight.

* * * * *